(12) United States Patent
Lin et al.

(10) Patent No.: US 10,251,428 B2
(45) Date of Patent: Apr. 9, 2019

(54) DRIVING MODULE FOR ELECTRONIC CIGARETTE

(71) Applicant: Microjet Technology Co., Ltd., Hsinchu (TW)

(72) Inventors: Ching-Sung Lin, Hsinchu (TW); Shih-Chang Chen, Hsinchu (TW); Li-Pang Mo, Hsinchu (TW); Chi-Jung Chen, Hsinchu (TW); Chi-Feng Huang, Hsinchu (TW); Hsuan-Kai Chen, Hsinchu (TW)

(73) Assignee: MICROJET TECHNOLOGY CO., LTD., Hsinchu (TW)

( * ) Notice: Subject to any disclaimer, the term of this patent is extended or adjusted under 35 U.S.C. 154(b) by 0 days.

(21) Appl. No.: 15/986,003

(22) Filed: May 22, 2018

(65) Prior Publication Data

US 2018/0360115 A1 Dec. 20, 2018

(30) Foreign Application Priority Data

Jun. 14, 2017 (TW) .............................. 106119765 A

(51) Int. Cl.
A24F 47/00 (2006.01)
A61M 15/06 (2006.01)
A61M 11/04 (2006.01)

(52) U.S. Cl.
CPC ......... *A24F 47/008* (2013.01); *A61M 11/042* (2014.02); *A61M 15/06* (2013.01)

(58) Field of Classification Search
CPC .... A24F 47/004–47/008; A61M 15/06; A61M 11/042–11/044

(Continued)

(56) References Cited

U.S. PATENT DOCUMENTS 10,111,281 B2 * 10/2018 Qiu ....................... A24F 47/008
2006/0047368 A1 3/2006 Maharajh et al.
(Continued)

FOREIGN PATENT DOCUMENTS

CN 1467376 A 1/2004
CN 201319860 Y 10/2009
(Continued)

OTHER PUBLICATIONS

Extended European Search Report dated Nov. 13, 2018 for Application No. 18173695.0.

*Primary Examiner* — Gary L Laxton
*Assistant Examiner* — Peter Novak
(74) *Attorney, Agent, or Firm* — Birch, Stewart, Kolasch & Birch, LLP

(57) ABSTRACT

A driving module for an electronic cigarette is provided. The electronic cigarette includes a casing, a mouthpiece, a sensing unit, an atomization component, a liquid storage component and a fluid transportation device. The driving module includes a battery, a connection interface, a power board and a control board. According to a control signal, a voltage of the driving power is converted into a specified voltage, and a driving signal is generated according to the specified voltage. According to the driving signal, the driving power with the specified voltage value is provided to the fluid transportation device to enable the fluid transportation device to transfer the cigarette liquid to the atomization component, and the driving power with the specified voltage value is provided to the atomization component to enable the atomization component to atomize the cigarette liquid and generate an atomized vapor.

19 Claims, 17 Drawing Sheets

(58) Field of Classification Search
 USPC .................................................. 131/329–230
 See application file for complete search history.

(56) References Cited

U.S. PATENT DOCUMENTS

| | | |
|---|---|---|
| 2008/0230052 A1 | 9/2008 | Montaser |
| 2012/0090630 A1* | 4/2012 | Hon ...................... A24F 47/002 |
| | | 131/273 |
| 2012/0111347 A1* | 5/2012 | Hon ...................... A24F 47/008 |
| | | 131/329 |
| 2015/0090277 A1* | 4/2015 | Xiang ................... A24F 47/008 |
| | | 131/328 |
| 2016/0143359 A1* | 5/2016 | Xiang ................... H05B 1/0227 |
| | | 392/387 |
| 2016/0213065 A1 | 7/2016 | Wensley et al. |

FOREIGN PATENT DOCUMENTS

| | | |
|---|---|---|
| CN | 201379072 Y | 1/2010 |
| CN | 102940313 A | 2/2013 |
| CN | 204907944 U | 12/2015 |
| TW | 200534801 A | 11/2005 |
| TW | 201010795 A | 3/2010 |
| WO | WO 2017/011419 A1 | 1/2017 |

\* cited by examiner

DRIVING MODULE FOR ELECTRONIC CIGARETTE

FIELD OF THE INVENTION

The present disclosure relates to a driving module, and more particularly to a driving module for an electronic cigarette.

BACKGROUND OF THE INVENTION

Nowadays, electronic cigarettes are gradually used to replace the conventional tobacco cigarettes. As shown in FIGS. 1A and 1B, the electronic cigarette includes a casing 1 and components which may be assembled and installed therein. Having a length and a diameter similar to the conventional tobacco cigarette, the casing 1 includes a first casing 1a and a second casing 1b, which may be thin-wall metal pipes, such as stainless steel pipes. The components of the electronic cigarettes include a driving module 2, a sensing unit 3, an atomization component 4 and a liquid storage component 5. The driving module 2 and the sensing unit 3 are disposed within the first casing 1a, while the first casing 1a has at least one entrance 1c adjacent to the sensing unit 3. The atomization component 4 and the liquid storage component 5 are disposed within the second casing 1b. The atomization component 4 is fixed on a bracket 7 and supported thereby. The atomization component 4 includes an electric heater 41, a liquid receiving part 42 sleeving on the electric heater 41 and a liquid transfer part 43 cooperating intimately with the liquid receiving part 42. The electric heater 41 is a hollow part. The liquid storage component 5 is disposed within the second casing 1b and has a passageway 51 for allowing gas to pass therethrough. The passageway 51 is surrounded with the liquid container 52. The liquid transfer part 43 sleeves on the liquid receiving part 42. Since the communication part 431 of the liquid transfer part 43 is contacted with the liquid container 52, the cigarette liquid in the liquid container 52 can be absorbed to or infiltrate to the liquid receiving part 42. Moreover, an intake-and-electric-connection element 10 is arranged between the atomization component 4 and the sensing unit 3, and the intake-and-electric-connection element 10 is in communication with the passageway 51 of the liquid storage component 5, so that an airflow path from the entrance 1c to the passageway 51 is defined. The gas introduced into the entrance 1c will move along the airflow path, passing through the sensing unit 3, the intake-and-electric-connection element 10 and the electric heater 41, then being introduced into the passageway 51 of the liquid storage component 5. The intake-and-electric-connection element 10 may be used for electrical connection and circulation of air flow. The electronic cigarette further includes an electrode ring 8. The electrode ring 8 is electrically connected with two pins (not shown) of the electric heater 41. Moreover, the electrode ring 8 is electrically connected with the driving module 2, through the electric connection between the intake-and-electric-connection element 10 and the sensing unit 3. The electric circuit of the electronic cigarette is selectively enabled or disabled according to the result of sensing the airflow by the sensing unit 3. Moreover, a mouthpiece 9 is disposed on an end of the second casing 1b and in communication with the passageway 51 of the liquid storage component 5. When the user inhales through the mouthpiece 9, which forms an airflow going through the inside of the electronic cigarette, the electric circuit of the electronic cigarette is enabled according to the detection of the airflow by sensing unit 3. The electric heater 41 is activated and then performs a heating operation. When the user stops inhaling, the gas in the electronic cigarette stops flowing, and the electric circuit of the electronic cigarette is disabled according to the sensing result of the sensing unit 3. More specifically, as mentioned above, the cigarette liquid in the liquid container 52 can be absorbed to or infiltrate to the liquid receiving part 42 through the communication part 431 of the liquid transfer part 43. When the user inhales through the mouthpiece 9, which forms an airflow going through the inside of the electronic cigarette, the electric circuit of the electronic cigarette is enabled according to the detection of the airflow by the sensing unit 3. Then, the driving module 2 provides electric power to the electrode ring 8 to activate the electric heater 41 to perform the heating operation. Consequently, the cigarette liquid absorbed to or infiltrate to the liquid receiving part 42 is heated and atomized by the electric heater 41, and the user can inhale the atomized vapor from the passageway 51 of the liquid storage component 5 through the mouthpiece 9.

As mentioned above, the cigarette liquid is transferred to the liquid receiving part 42 through the communication part 431 of the liquid transfer part 43. However, this design has some drawbacks. First, since it is difficult to precisely control the amount of liquid infiltration from the communication part 431 of the liquid transfer part 43, the cigarette liquid usually fails to be transferred uniformly to the liquid receiving part 42. If a part of the liquid receiving part 42 receives a lesser amount of the cigarette liquid than the other parts, the liquid droplets are not uniformly generated so that an unpleasing burning taste appears in the atomized vapor. Second, since the amount of liquid infiltration from the communication part 431 of the liquid transfer part 43 to be transferred to the liquid receiving part 42 cannot be precisely controlled, the liquid leakage occurs. Especially when the mouthpiece 9 stays in the upright position vertical to the ground, the cigarette liquid continuously moves from the liquid container 52 to the liquid receiving part 42 under the force of gravity. Once the liquid receiving part 42 reaches a saturation state, the excessive cigarette liquid drops down to the intake-and-electric-connection element 10. Moreover, the cigarette liquid may drop down through the sensing unit 3 and leak out from the at least one entrance 1c, which results in terrible user experience.

Moreover, there are some differences between the electronic cigarettes and the real cigarettes. For example, when people smoke the real cigarettes, they are accustomed to smoking quickly, shortly and laboriously. Whereas, people smoke the electronic cigarettes lengthily and gently. While the user smokes the real cigarette and inhales a great amount of oxygen gas, the user can quickly get the wanted amount of smoke because the tobacco is burnt and atomized faster. However, while the user smokes the conventional electronic cigarette, the electric power to be transmitted to the electric heater and the heating speed cannot be adjusted. That is, if the heating speed is too fast, the cigarette liquid is atomized by the atomization component very quickly. Since the cigarette liquid of the conventional electronic cigarette is provided according to a siphon effect, the speed of providing the cigarette liquid is too slow and thus cannot catch up the heating speed. Under this circumstance, the amount of the atomized vapor is insufficient or the atomization component is burnt out. Since the electric power transmitted to the atomization component of the conventional electronic cigarette is fixed, the user has to smoke the electronic cigarette lengthily and gently to provide a sufficient heating time to the atomization component. That is, the conventional method of atomizing the cigarette liquid of the electronic cigarette still has some drawbacks. The above problems lead to significant differences between the real cigarette and the electronic cigarette. Because of these drawbacks, the user does not prefer to choose the electronic cigarette in replace of the real cigarette.

For solving the drawbacks of the conventional technologies, the present disclosure provides an improved driving module for an electronic cigarette.

SUMMARY OF THE INVENTION

An object of the present disclosure provides a driving module for an electronic cigarette. The cooperation of a fluid transportation device, an atomization component and the driving module forms a controllable switch element, so that the amount of the cigarette liquid to be transferred to the liquid receiving part of the atomization component is precisely controlled by the controllable switch element. Consequently, the taste of the atomized vapor is enhanced, and the liquid leakage problem is solved. Moreover, according to the result of detecting the pressure of the airflow, the driving frequency of the fluid transportation device and the driving power of the heater module are correspondingly changed, and the speed of atomizing the cigarette liquid and the speed of providing the cigarette liquid are correspondingly adjusted. Therefore, the user can inhale a great amount of atomized vapor quickly, or the user can inhale the same amount of atomized vapor with each whiff.

An aspect of the present disclosure provides a driving module for an electronic cigarette containing a cigarette liquid. The electronic cigarette includes a casing, a mouthpiece, a sensing unit, an atomization component, a liquid storage component and a fluid transportation device. The driving module of the electronic cigarette includes a battery, a connection interface, a power board and a control board. The battery provides a driving power. The connection interface is electrically connected with the battery. The power board is electrically connected with the battery through the connection interface, and includes a voltage converter, a heater module and a voltage controller. The voltage converter is configured to adjust the magnitude of the voltage of the driving power, the heater module is configured to drive the atomization component to heat and atomize the cigarette liquid, and the voltage controller is configured to calculate a specified voltage value. The control board is electrically connected with the battery through the connection interface, and includes a microprocessor and a fluid driving unit. The microprocessor receives a control signal and issues a driving signal, and the fluid driving unit drives the fluid transportation device to transfer the cigarette liquid according to the driving signal. When the microprocessor receives the control signal from the sensing unit, the microprocessor controls the voltage controller to calculate the specified voltage value according to the control signal. After the specified voltage value is calculated, the microprocessor controls the voltage converter to convert a voltage of the driving power provided by the battery into the specified voltage. The microprocessor issues the driving signal to the fluid driving unit and the heater module such that the driving power with the specified voltage value is provided to the fluid transportation device and the atomization component by the fluid driving unit and the heater module respectively, thereby enabling the fluid transportation device to transfer the cigarette liquid to the atomization component which atomizes the cigarette liquid to generate an atomized vapor.

BRIEF DESCRIPTION OF THE DRAWINGS

Aspects of the present disclosure are best understood from the following detailed description when read with the accompanying figures. It is noted that, in accordance with the standard practice in the industry, various features are not drawn to scale. In fact, the dimensions of the various features may be arbitrarily increased or reduced for clarity of discussion.

DETAILED DESCRIPTION OF THE PREFERRED EMBODIMENT

The present disclosure will now be described more specifically with reference to the following embodiments. It is to be noted that the following descriptions of preferred embodiments of this invention are presented herein for purpose of illustration and description only. It is not intended to be exhaustive or to be limited to the precise form disclosed.

Figure 1A:
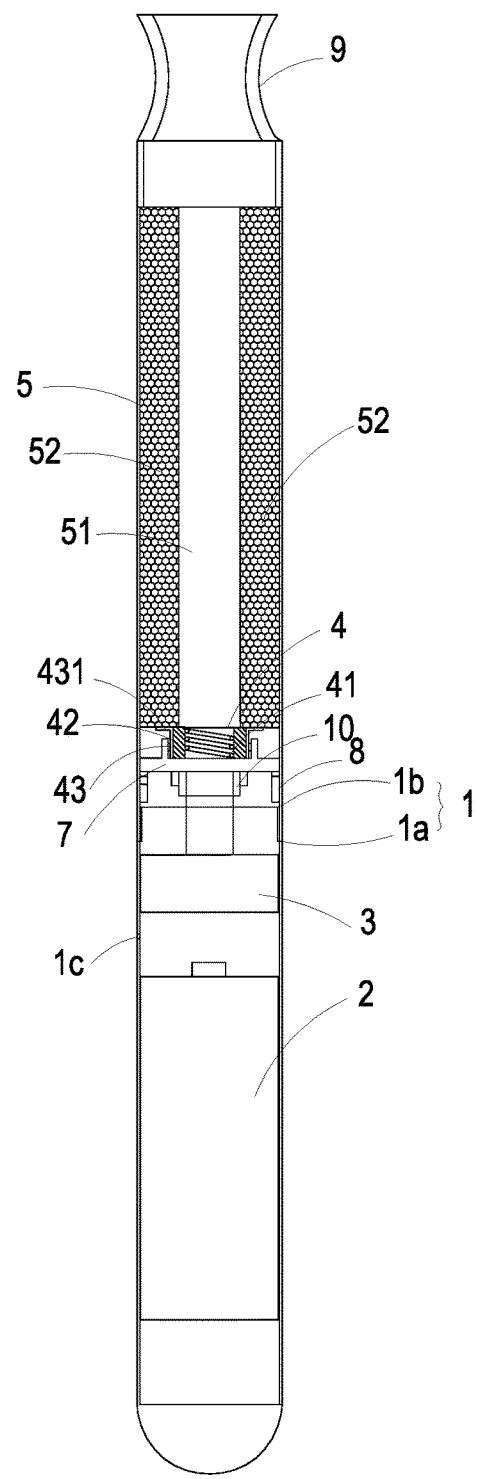
FIG. 1A is a schematic cross-sectional view illustrating a conventional electronic cigarette.
Figure 1B:
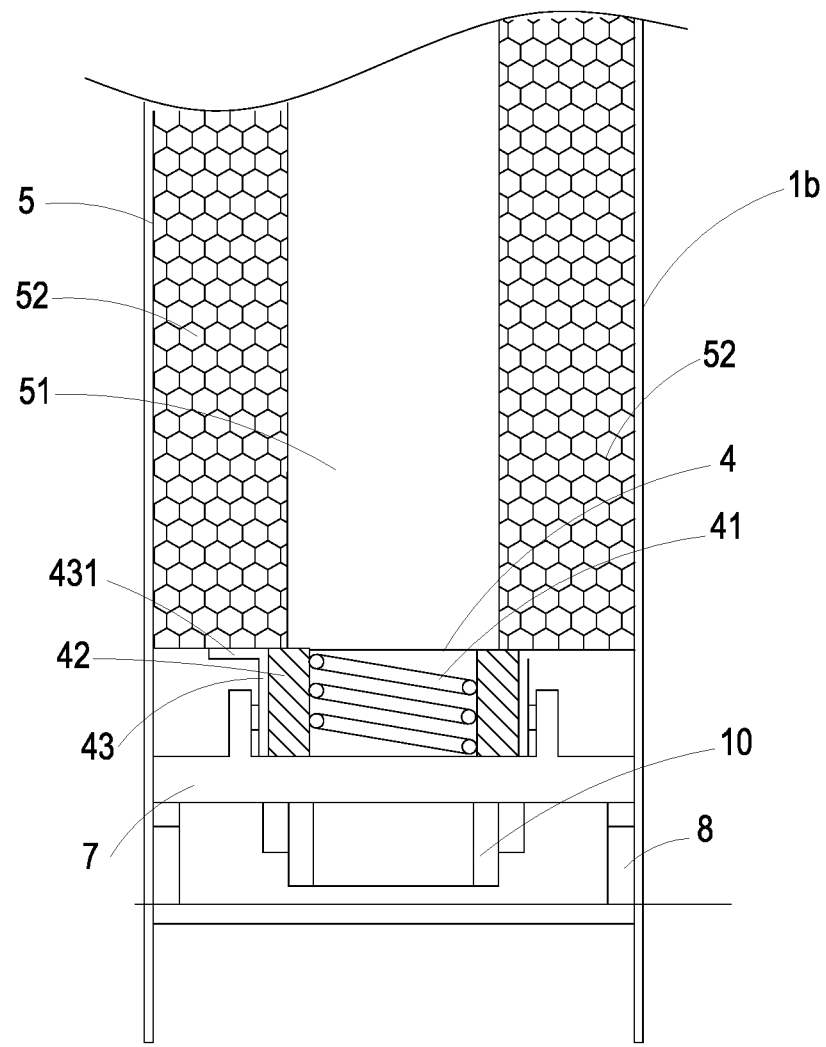
FIG. 1B is a partial enlarged view of the atomization component of the conventional electronic cigarette as shown in FIG. 1A.
Figure 2A:
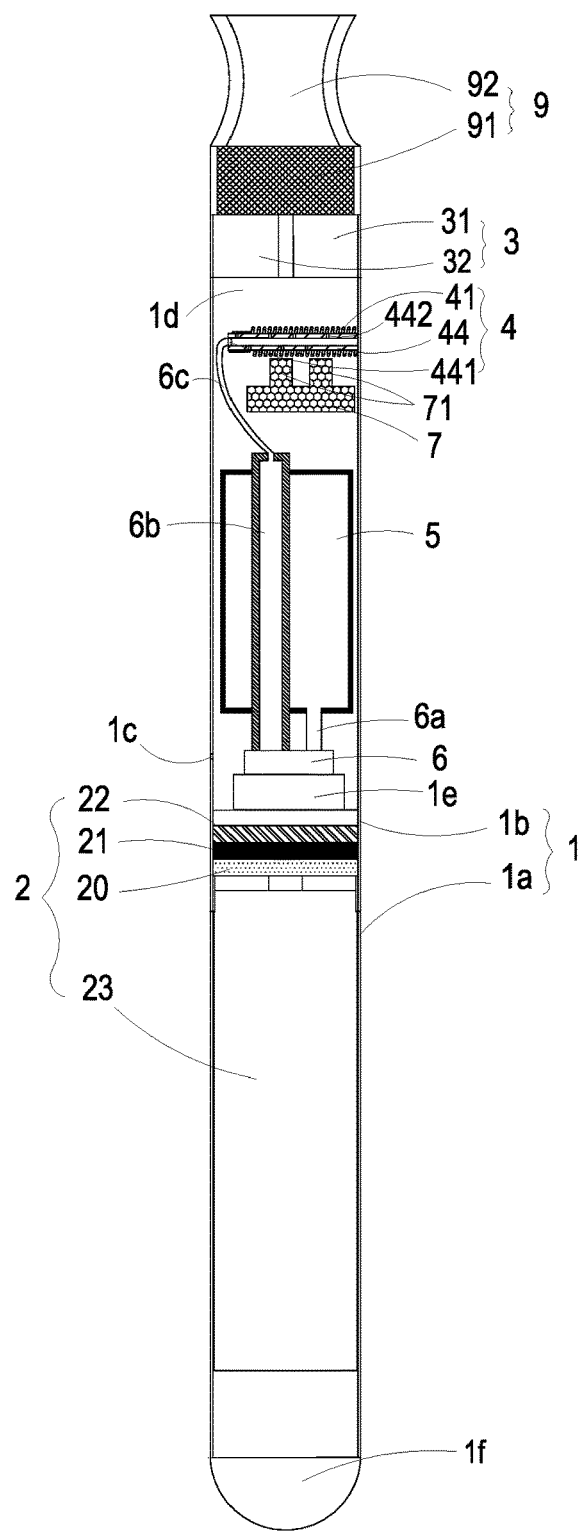
FIG. 2A is a schematic cross-sectional view illustrating an electronic cigarette according to an embodiment of the present disclosure.
Figure 2B:
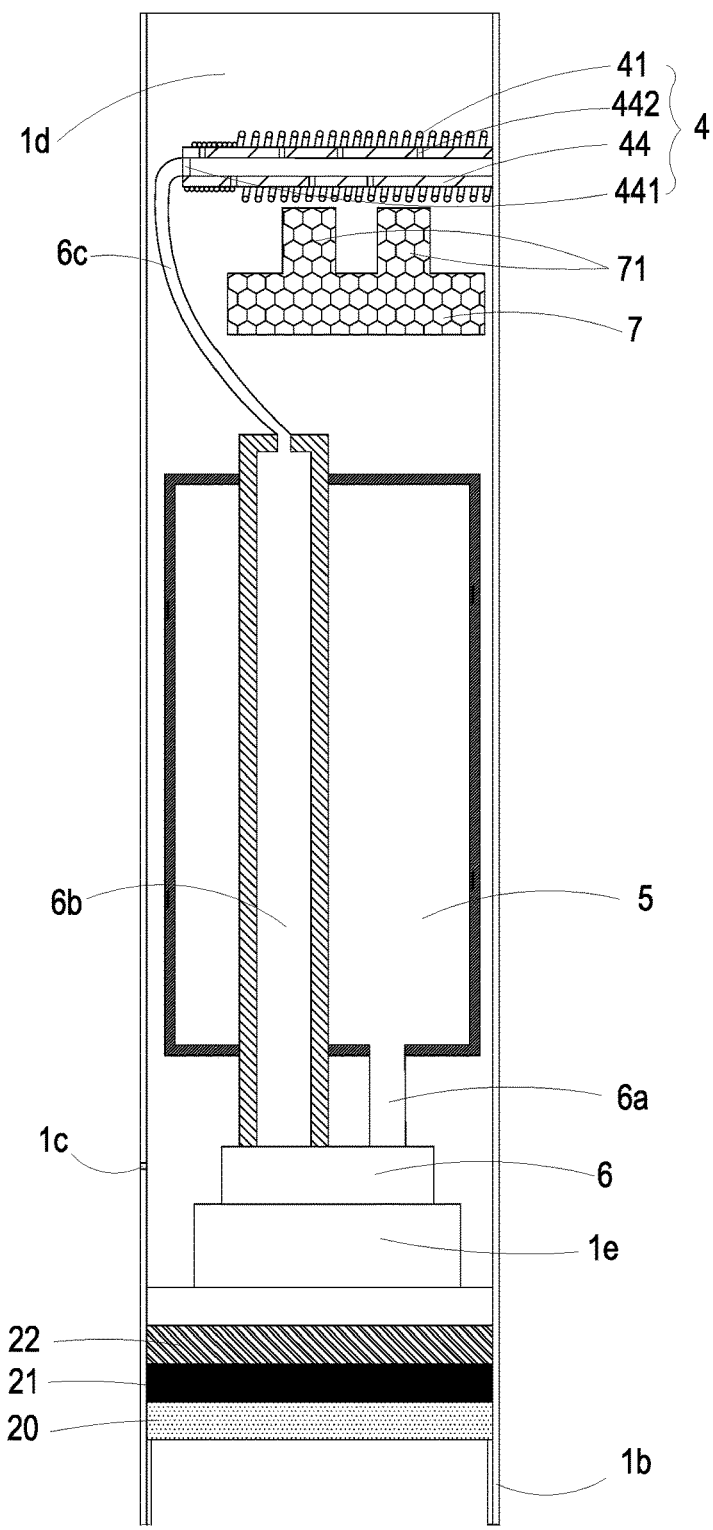
FIG. 2B is a partial enlarged view of the atomization component of the electronic cigarette as shown in FIG. 2A.
Figure 2C:
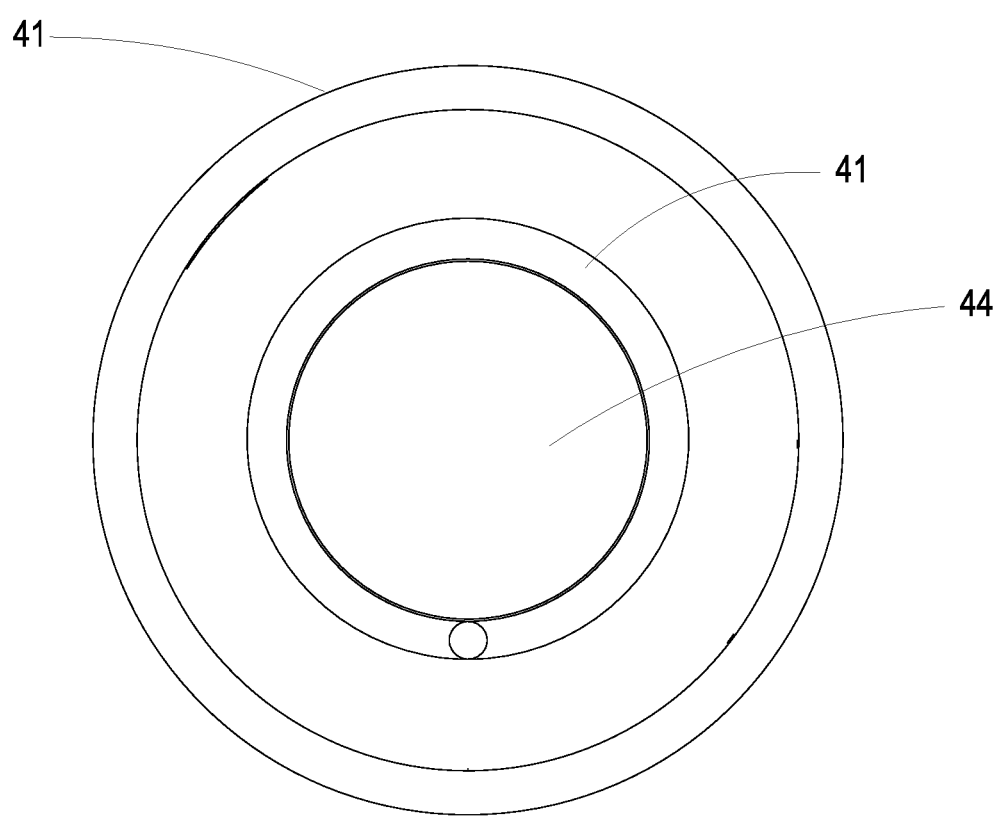
FIG. 2C is a partial enlarged view of the electronic cigarette in FIG. 2A.
Figure 3A:
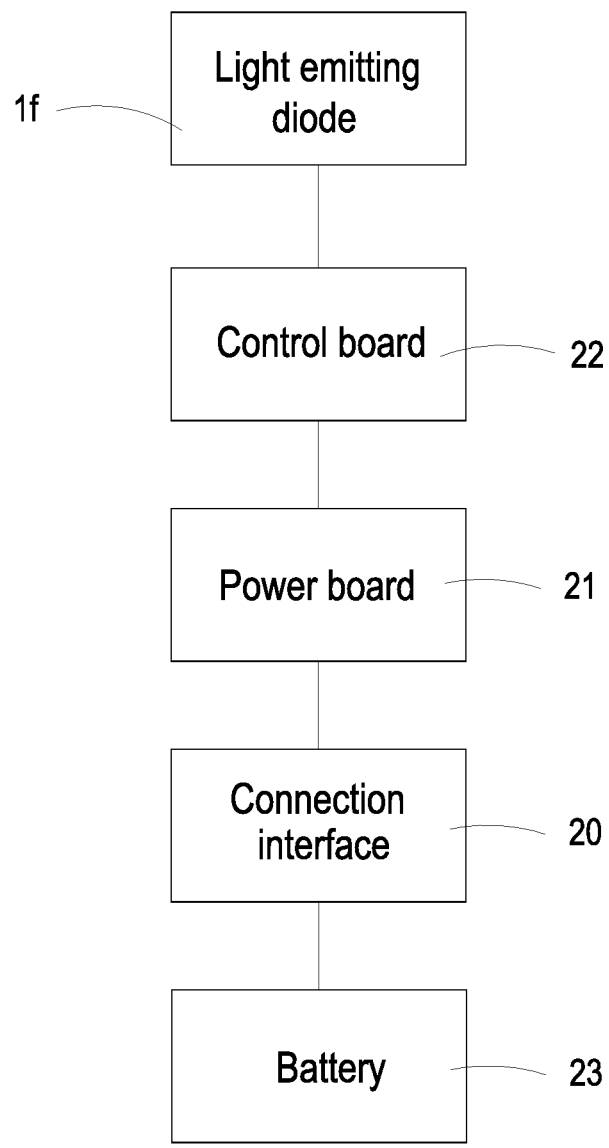
FIG. 3A is a schematic functional block diagram illustrating the driving module of the driving module according to the embodiment of the present disclosure.
Figure 3B:
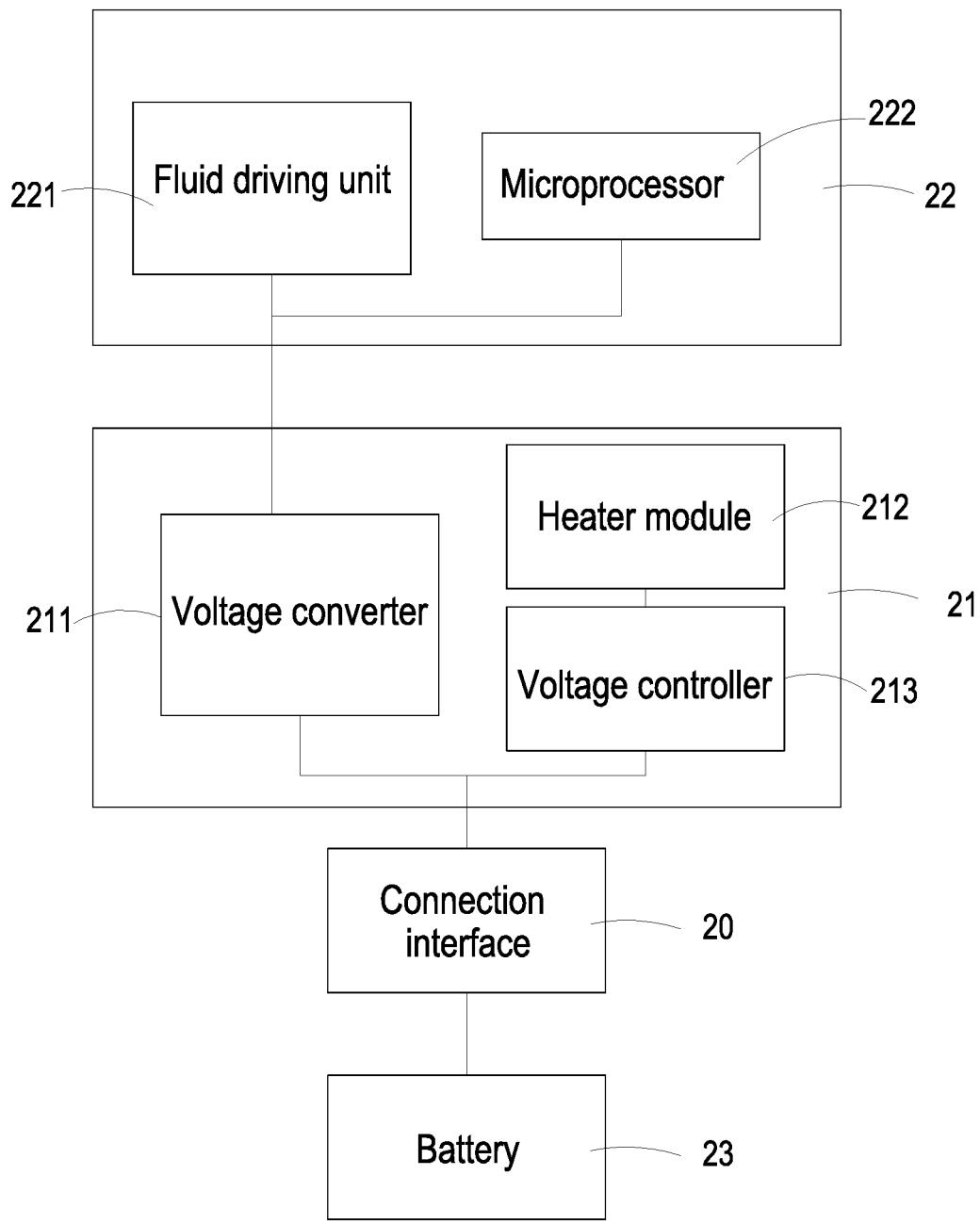
FIG. 3B is a schematic functional block diagram illustrating the connection interface, the power board and the control board of the driving module as shown in FIG. 3A.
Figure 3C:
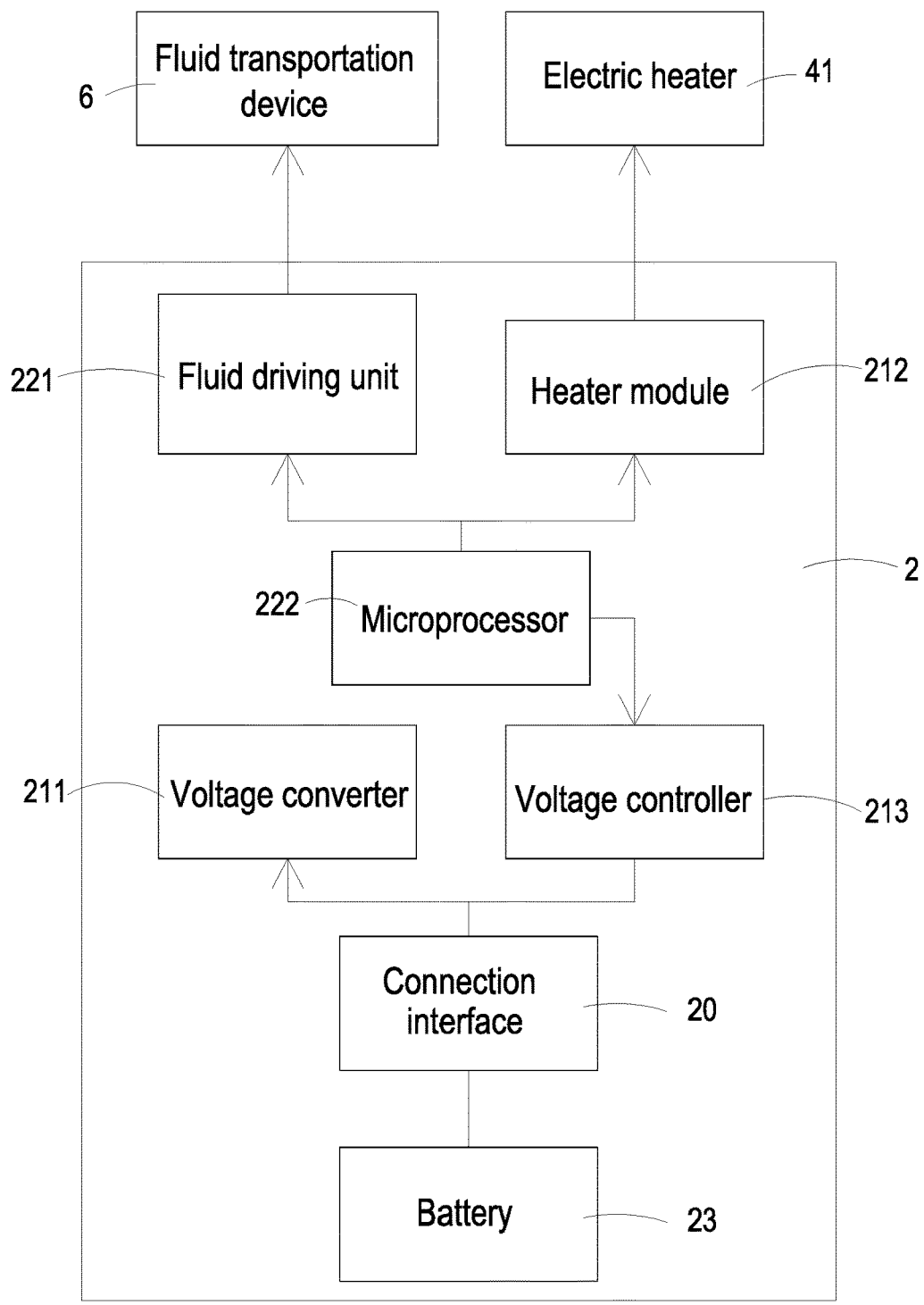
FIG. 3C is a schematic functional block diagram illustrating the signal transmission path of the driving module as shown in FIG. 3A.

FIG. 2A is a schematic cross-sectional view illustrating an electronic cigarette according to an embodiment of the present disclosure. FIG. 2B and FIG. 2C are partial enlarged views of the electronic cigarette in FIG. 2A. FIG. 3A is a schematic functional block diagram illustrating the driving module of the driving module according to the embodiment of the present disclosure. FIG. 3B is a schematic functional block diagram illustrating the connection interface, the power board and the control board of the driving module as shown in FIG. 3A. FIG. 3C is a schematic functional block diagram illustrating the signal transmission path of the driving module as shown in FIG. 3A.

As shown in FIGS. 2A, 2B, 2C, 3A, 3B and 3C, the electronic cigarette of the present disclosure includes a casing 1, a driving module 2, a sensing unit 3, an atomization component 4, a liquid storage component 5, a fluid transportation device 6, a bracket 7 and a mouthpiece 9. The casing 1 is an assembly of a first casing 1a and a second casing 1b, which are detachably engaged with each other. In an embodiment, the driving module 2 includes a connection interface 20, a power board 21, a control board 22 and a battery 23. The battery 23 is installed within the first casing 1a. The connection interface 20, the power board 21 and the control board 22 are installed within the second casing 1b. The power board 21 and the control board 22 are located over the connection interface 20. The power board 21 and the control board 22 are electrically connected with the battery 23 through the connection interface 20 of the driving module 2. Moreover, the first casing 1a and the second casing 1b are combined together through the connection interface 20. There is an airflow chamber 1d within the second casing 1b. Moreover, the sensing unit 3, the atomization component 4, the liquid storage component 5, the fluid transportation device 6 and the bracket 7 are disposed within the second casing 1b.

In one embodiment, the first casing 1a and the second casing 1b may be thin-wall metal pipes, such as stainless steel pipes. After the casing 1 is assembled by the first casing 1a and the second casing 1b, the length and diameter of the casing 1 are similar to those of the conventional tobacco cigarette. In one embodiment, at least one entrance 1c adjacent to the fluid transportation device 6 is disposed on a surface of the second casing 1b. After an ambient airflow is fed into the at least one entrance 1c, the airflow passes through the airflow chamber 1d, the sensing unit 3 and the mouthpiece 9 along an airflow path. In other embodiments, the position of the entrance 1c is not restricted as long as the entrance 1c is in communication with the airflow chamber 1d. Similarly, the ambient airflow passes through the entrance 1c, the airflow chamber 1d, the sensing unit 3 and the mouthpiece 9 along the airflow path, by which the atomized vapor is sequentially transferred through the airflow chamber 1d, the sensing unit 3 and the mouthpiece 9 and outputted from the second casing 1b. Consequently, the atomized vapor can be inhaled by the user.

In one embodiment, the mouthpiece 9 is located at an end of the second casing 1b. The sensing unit 3 is disposed within the second casing 1b. The sensing unit 3 is located near the mouthpiece 9 and in communication with the mouthpiece 9. The sensing unit 3 is used for sensing the airflow. According to the result of sensing the airflow, the driving power of the electronic cigarette is selectively enabled or disabled.

The atomization component 4 is perpendicularly disposed on an inner wall of the second casing 1b, and located near the sensing unit 3. The atomization component 4 includes an electric heater 41 and a liquid guiding tube 44. The electric heater 41 defines a hollow part for allowing the gas to go through. The two pins (not shown) of the electric heater 41 are electrically connected with the driving module 2 through the connection interface 20. According to a state of the airflow detected by the sensing unit 3, the electric heater 41 is controlled to selectively heat or stop heating. The liquid guiding tube 44 is used for guiding the cigarette liquid. For example, the liquid guiding tube 44 may be stainless steel or a heat-resistant material. A front end of the liquid guiding tube 44 has an input port 441. Moreover, plural perforations 442 are formed in a tube wall of the liquid guiding tube 44. The electric heater 41 is arranged around the liquid guiding tube 44. After the cigarette liquid is heated and atomized by the electric heater 41, an atomized vapor is generated to be smoked by the user. In one embodiment, the liquid transfer tube 6c is a flexible tube capable of withstanding high temperature. Through the liquid transfer tube 6c, the fluid transportation device 6 is in communication with the atomization component 4 without being hindered by the bracket 7 within the airflow chamber 1d. In case that the flexible tube is used as the liquid transfer tube 6c, the liquid transfer tube 6c can be easily assembled or disassembled. Consequently, the flexibility of maintaining the electronic cigarette is increased.

In one embodiment, the bracket 7 is disposed within the second casing 1b and connected with the inner wall of the second casing 1b. The bracket 7 includes two supporting parts 71. The atomization component 4 is disposed and fixed on the two supporting parts 71. The supporting parts 71 are connected with the atomization component 4 to provide a supporting force to the atomization component 4. The example of the bracket 7 is presented herein for purpose of illustration and description only. Since the atomization component 4 is supported by the two supporting parts 71, the contact area between the bracket 7 and the atomization component 4 is reduced. That is, the distribution area of the electric heater 41 around the liquid guiding tube 44 is increased, thereby enhancing the efficiency of atomization (e.g., thermal atomization).

In one embodiment, the liquid storage component 5 is disposed within the second casing 1b for storing the cigarette liquid. The fluid transportation device 6 is disposed within the second casing 1b and located at a bottom portion of the liquid storage component 5. The fluid transportation device 6 includes an input channel 6a, an output channel 6b and a liquid transfer tube 6c. The input channel 6a is in communication with the liquid storage component 5. The output channel 6b runs through the liquid storage component 5. The output channel 6b is in communication with the input port 441 of the liquid guiding tube 44 of the atomization component 4 through the liquid transfer tube 6c. In accordance with a feature of the present disclosure, the fluid transportation device 6 is used as a on-off switch element for selectively allowing the cigarette liquid from the liquid storage component 5 to pass through. The fluid transportation device 6 is positioned in the second casing 1b and supported by a supporting seat 1e.

In an embodiment, the power board 21 of the driving module 2 includes a voltage converter 211, a heater module 212 and a voltage controller 213. The voltage converter 211 is used for adjusting the magnitude of the voltage of the driving power. The heater module 212 is used for driving the electric heater 41 of the atomization component 4 to heat and atomize the cigarette liquid. The voltage controller 213 is used for calculating a specified voltage value.

In one embodiment, the control board 22 further includes a microprocessor 222 and a fluid driving unit 221. The microprocessor 222 receives a control signal and issues a driving signal. According to the driving signal, the fluid driving unit 221 drives the fluid transportation device 6 to transfer the cigarette liquid. In one embodiment, when the microprocessor 222 receives the control signal, the microprocessor 222 controls the voltage controller 213 to calculate the specified voltage value according to the control signal. After the specified voltage value is calculated, the voltage of the driving power from the battery 23 is converted into the specified voltage by the voltage converter 211 through the connection interface 20 under control of the microprocessor 222. The microprocessor 222 issues the driving signal to the fluid driving unit 221 and the heater module 212. Consequently, the driving power with the specified voltage value is provided to the fluid transportation device 6 and the electric heater 41 of the atomization component 4 through the fluid driving unit 221 and the heater module 212, respectively. Consequently, the fluid driving unit 221 drives the fluid transportation device 6 to transfer the cigarette liquid and drives the electric heater 41 of the atomization component 4 to atomize the cigarette liquid. Since the power board 21 and the control board 21 of the driving module 2 are capable of adjusting the voltage value of the driving power, the battery 23 of the driving module 2 with any appropriate voltage is feasible. Moreover, the specified voltage value is determined according to the airflow condition. As the voltage of the driving power is changed, the driving power applied to the fluid transportation device 6 and the electric heater 41 is adjusted. Correspondingly, the transferring speed of the fluid transportation device 6 and the atomizing speed of the electric heater 41 are changed. Consequently, while the user smokes the electronic cigarette, the user can inhale each whiff of the atomized vapor at the same concentration regardless of the inhaling speed. Consequently, the taste of inhaling the atomized vapor is enhanced.

In one embodiment, an example of the battery 23 of the driving module 2 includes but is not limited to a rechargeable battery or a disposable battery. In one embodiment, moreover, the first casing 1a along with the battery 23 of the driving module 2 is detachable. Consequently, the electronic cigarette is portable for convenience. If the electric power of the battery 23 of the driving module is insufficient, the battery 23 can be easily replaced with a new one. Then the first casing 1a and the second casing 1b are assembled with each other through the connection interface 20, by which the electronic cigarette can be normally reoperated.

In an embodiment, the sensing unit 3 includes but not limited to an airflow sensor 31 and an air pressure sensor 32. The airflow sensor 31 issues a control signal to the driving module 2 according to the result of detecting the airflow. Consequently, the driving power from the driving module 2 is selectively enabled or disabled according to the result of detecting the airflow by the sensing unit 3. Changes in air pressure may be monitored by the air pressure sensor 32, thereby adjusting the speed of atomization and liquid supply. More specifically, the air pressure sensor 32 adjusts the control signal for the driving module 2 by detecting the changes in air pressure as the user sucks air through the electric cigarette. Therefore, a driving frequency of the fluid transportation device 6 is adjusted to change a speed of providing the cigarette liquid, and a driving power used for the atomization component 4 is also adjusted to change a speed of atomizing the cigarette liquid, in accordance with the control signal.

In one embodiment, when the sensing unit 3 detects the airflow, the sensing unit 3 issues the control signal to the driving module 2 according to the pressure of the airflow. According to the control signal, the fluid transportation device 6 is enabled. Consequently, the cigarette liquid is transmitted from the liquid storage component 5 to the input channel 6a, and outputted from the output channel 6b to the liquid guiding tube 44 of the atomization component 4 through the liquid transfer tube 6c. The cigarette liquid is outputted from the liquid guiding tube 44 through the perforations 442. Since the fluid transportation device 6 is used as a switch element, the cigarette liquid is transferred to the electric heater 41 of the atomization component 4 through the fluid transportation device 6 at a fixed quantity. After the cigarette liquid is heated and atomized by the electric heater 41, the atomized vapor is generated. When the user inhales the atomized vapor through the bore 92 of the mouthpiece 9, the airflow is fed into the airflow path through the at least one entrance 1c. Consequently, the internal pressure and the external pressure of the casing 1 are balanced. On the contrary, when the user stops smoking, the airflow does not flow through the electronic cigarette. According to the sensing result of the sensing unit 3, which stops issuing the control signal, the electric circuit of the electronic cigarette is disabled. Accordingly, since the cigarette liquid is transferred to the electric heater 41 of the atomization component 4 at the fixed quantity, the user can inhale a great amount of atomized vapor quickly and inhale the same amount and concentration of atomized vapor with each whiff. Consequently, the taste of the atomized vapor is enhanced.

The electronic cigarette further includes a light emitting diode 1f. The light emitting diode 1f is located at a front end of the first casing 1a. The light emitting diode 1f is powered by the battery 23 of the driving module 2. Under control of the control board 22, the light emitting diode 1f is selectively in an on state or an off state to provide a prompt message. Alternatively, under control of the control board 22, a luminance of the light emitting diode 1f is adjusted to indicate a flow condition of the atomized vapor.

Please refer to FIG. 2A again. The mouthpiece 9 is located at an end of the second casing 1b. Moreover, the mouthpiece 9 is in communication with the airflow chamber 1d. The mouthpiece 9 includes a filter 91 and a bore 92. The filter 91 is located at an end of the second casing 1b so as to stuff an opening between the mouthpiece 9 and the bore 92. In case that the cigarette liquid is not atomized completely, the cigarette liquid is stopped by the filter 91, thereby forming a preventive measure from inhalation. Consequently, the incompletely atomized cigarette liquid cannot be inhaled by the user.

Figure 4:
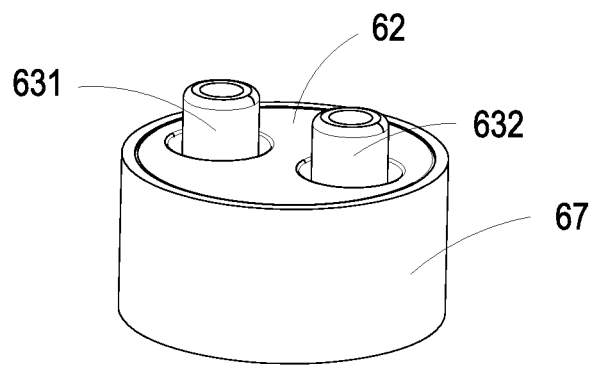
FIG. 4 is a schematic perspective view illustrating the fluid transportation device of the driving module according to the embodiment of the present disclosure.
Figure 5A:
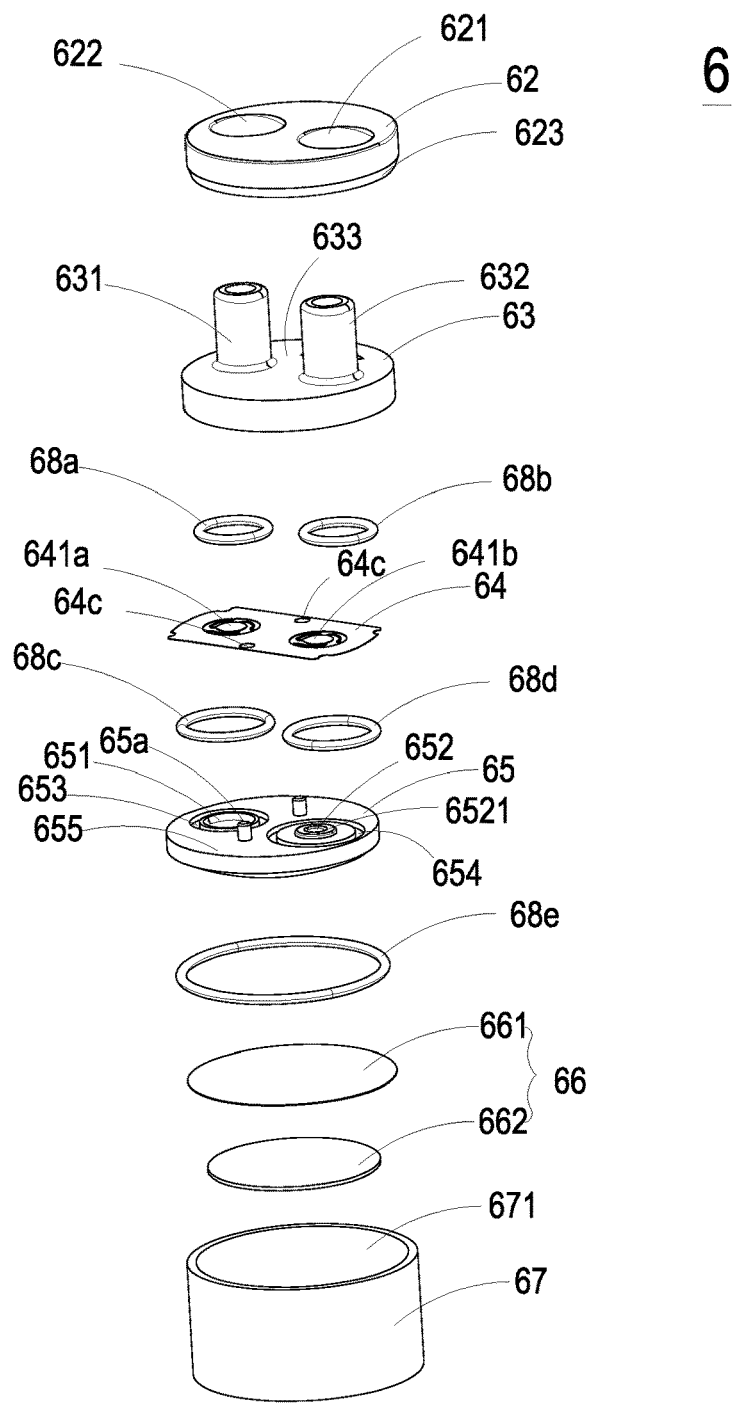
FIG. 5A is a schematic exploded view illustrating the fluid transportation device of FIG. 4 and taken along a front side.
Figure 5B:
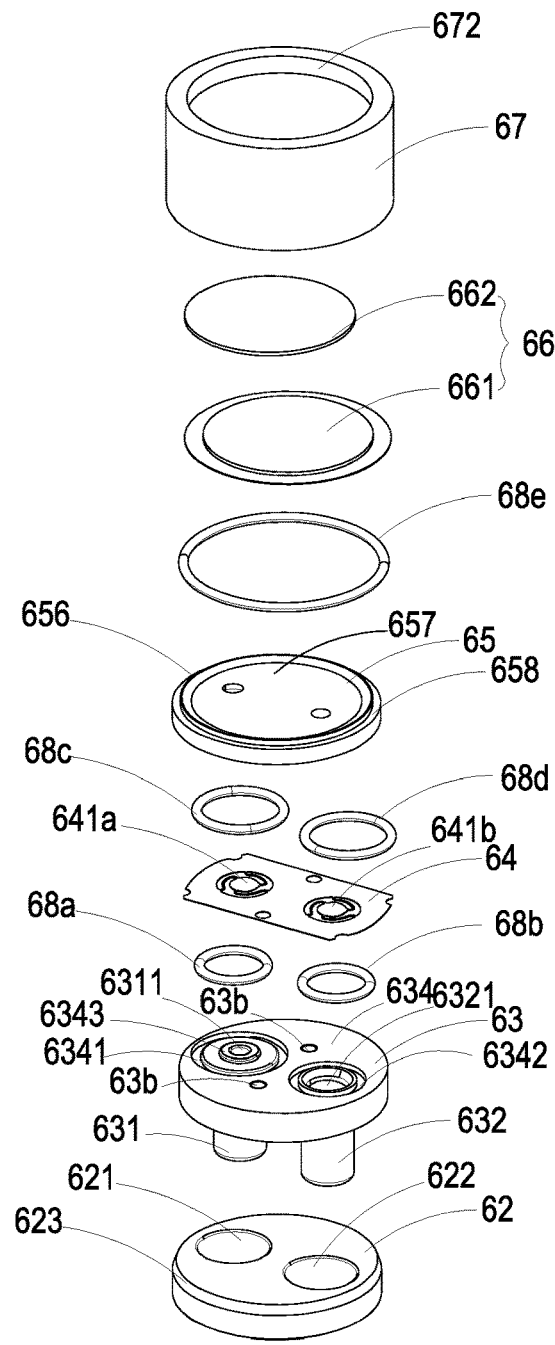
FIG. 5B is a schematic exploded view illustrating the fluid transportation device of FIG. 4 and taken along a rear side.
Figure 6A:
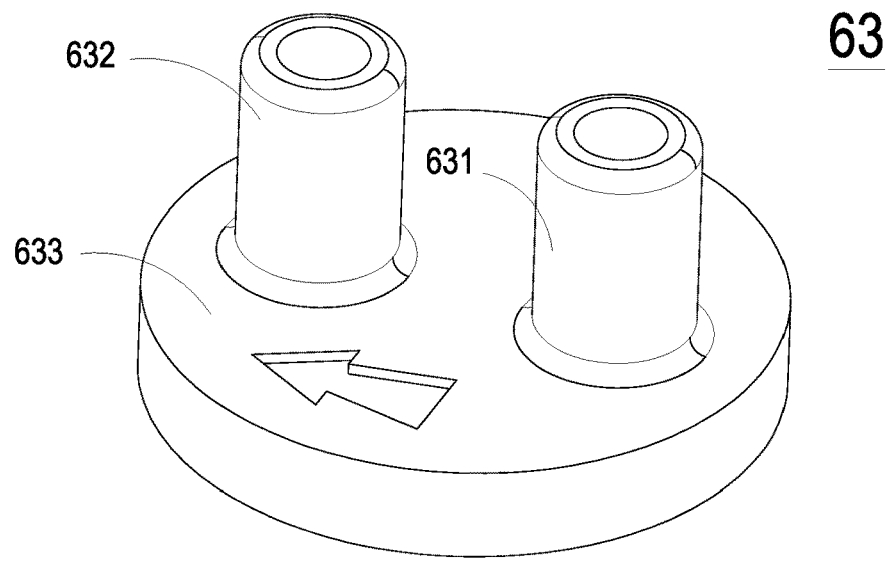
FIG. 6A is a schematic perspective view illustrating the valve body of the fluid transportation device of FIG. 4 and taken along the front side.
Figure 6B:
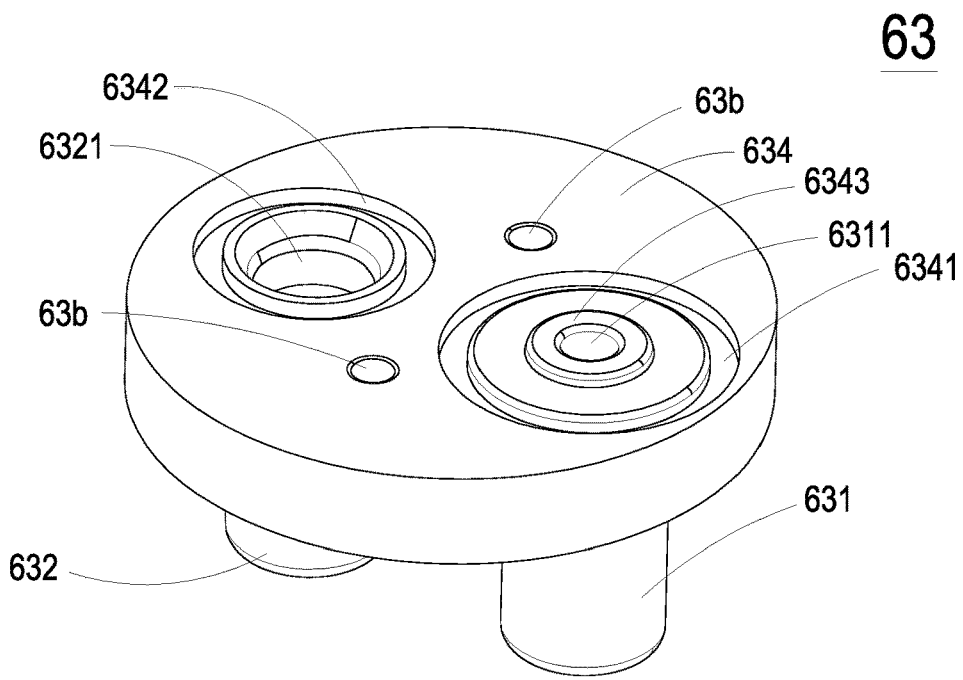
FIG. 6B is a schematic perspective view illustrating the valve body of the fluid transportation device of FIG. 4 and taken along the rear side.
Figure 7A:
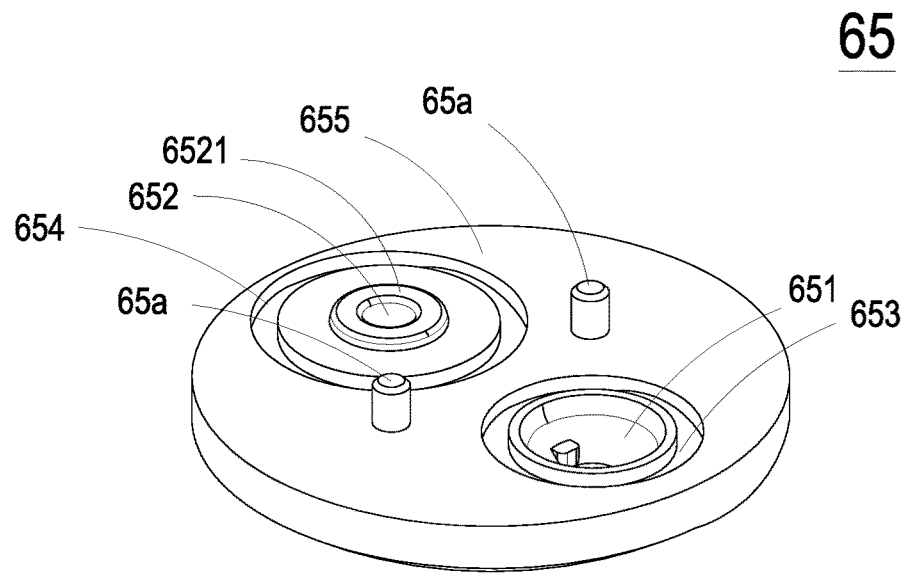
FIG. 7A is a schematic perspective view illustrating the valve chamber seat of the fluid transportation device of FIG. 4 and taken along the front side.
Figure 7B:
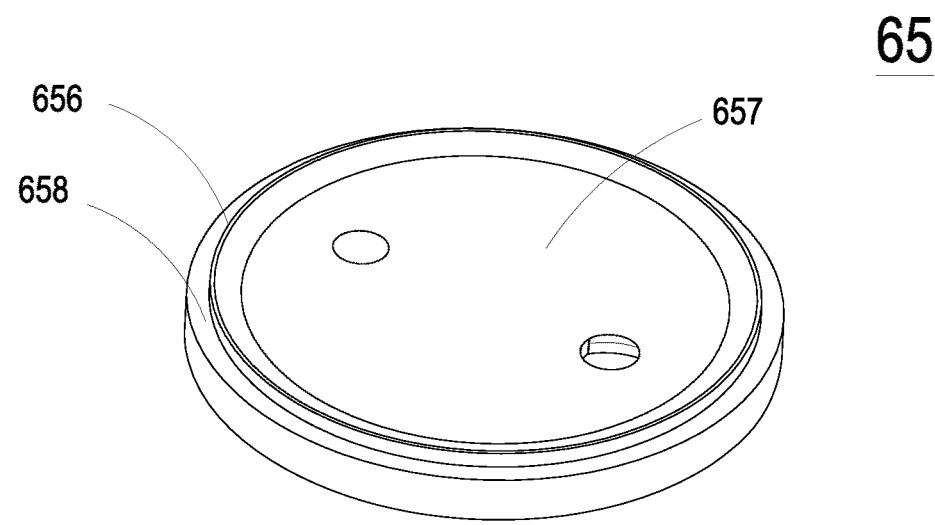
FIG. 7B is a schematic perspective view illustrating the valve chamber seat of the fluid transportation device of FIG. 4 and taken along the rear side.

FIG. 4 is a schematic perspective view illustrating the fluid transportation device of the driving module according to the embodiment of the present disclosure. FIG. 5A is a schematic exploded view illustrating the fluid transportation device of FIG. 4 and taken along a front side. FIG. 5B is a schematic exploded view illustrating the fluid transportation device of FIG. 4 and taken along a rear side. FIG. 6A is a schematic perspective view illustrating the valve body of the fluid transportation device of FIG. 4 and taken along the front side. FIG. 6B is a schematic perspective view illustrating the valve body of the fluid transportation device of FIG. 4 and taken along the rear side. FIG. 7A is a schematic perspective view illustrating the valve chamber seat of the fluid transportation device of FIG. 4 and taken along the front side. FIG. 7B is a schematic perspective view illustrating the valve chamber seat of the fluid transportation device of FIG. 4 and taken along the rear side.

Please refer to FIGS. 4, 5A, 5B, 6A, 6B, 7A and 7B. The fluid transportation device 6 includes a valve body 63, a valve membrane 64, a valve chamber seat 65, an actuator 66 and an outer sleeve 67. After the valve body 63, the valve membrane 64, the valve chamber seat 65 and the actuator 66 are sequentially stacked on each other, the combination of the valve body 63, the valve membrane 64, the valve chamber seat 65 and the actuator 66 is accommodated within the outer sleeve 67 and assembled with the outer sleeve 67.

The valve body 63 and the valve chamber seat 65 are the main components for guiding the cigarette liquid to be inputted into or outputted from of the fluid transportation device 6. The valve body 63 includes an inlet passage 631 and an outlet passage 632. The inlet passage 631 and the outlet passage 632 run through a first surface 633 and a second surface 634 of the valve body 63. An inlet opening 6311 is formed in the second surface 634 and in communication with the inlet passage 631. Moreover, a groove 6341 is formed in the second surface 634 and arranged around the inlet opening 6311. A protrusion block 6343 is disposed on the periphery of the inlet opening 6311. An outlet opening 6321 is formed in the second surface 634 and in communication with the outlet passage 632. A groove 6342 is arranged around the outlet opening 6321. Moreover, plural recesses 63b are formed on the second surface 634 of the valve body 63.

The valve chamber seat 65 includes a third surface 655, a fourth surface 656, plural posts 65a, an inlet valve channel 651, an outlet valve channel 652 and a pressure chamber 657. The plural posts 65a are formed on the third surface 655. The posts 65a are aligned with the corresponding recesses 63b of the valve body 63. When the posts 65a are inserted into the corresponding recesses 63b of the valve body 63, the valve body 63 and the valve chamber seat 65 are combined together. The inlet valve channel 651 and the outlet valve channel 652 run through the third surface 655 and the fourth surface 656. A groove 653 is formed on the third surface 655 and arranged around the inlet valve channel 651. A protrusion block 6521 is disposed on the third surface 655 around the periphery of the outlet valve channel 652. A groove 654 is formed on the third surface 655 and arranged around the outlet valve channel 652. The pressure chamber 657 is concavely formed on the fourth surface 656, and in communication with the inlet valve channel 651 and the outlet valve channel 652. Moreover, a concave structure 658 is formed on the periphery of the fourth surface 656 outside the pressure chamber 657.

Figure 8:
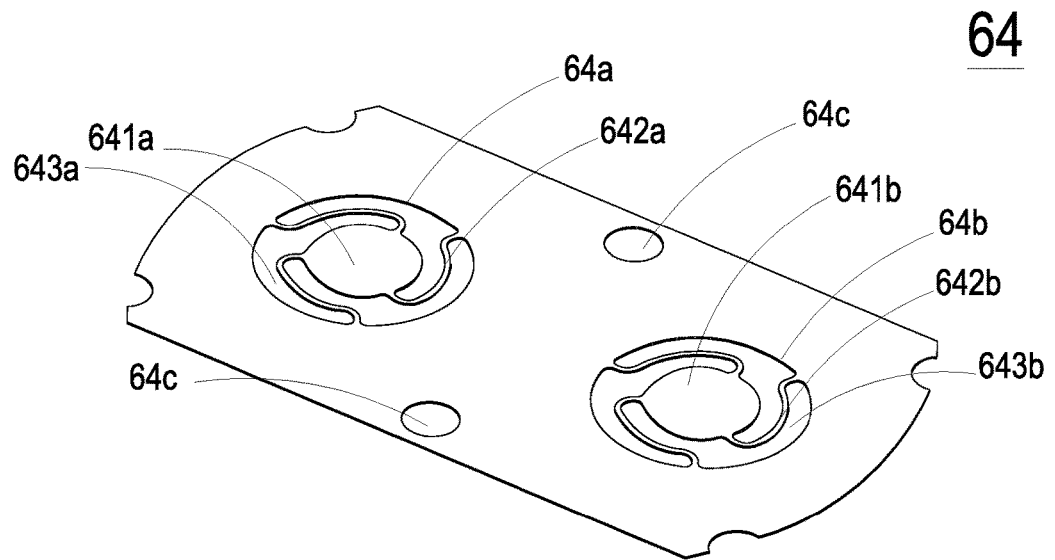
FIG. 8 is a schematic top view illustrating the valve membrane of the fluid transportation device of FIG. 4.

FIG. 8 is a schematic top view illustrating the valve membrane of the fluid transportation device of FIG. 4. Please refer to FIGS. 5A, 5B and 8. In an embodiment, the valve membrane 64 is made of polyimide (PI), and the valve membrane 64 is produced by a reactive ion etching (RIE) process, in which a photosensitive photoresist is applied to a valve substrate, a pattern of a valve structure is formed after exposure and development of the valve substrate, and then the polyimide layer uncovered by the photoresist is etched so that the valve structure of the valve membrane 64 is formed. The valve membrane 64 is a flat thin film structure. As shown in FIG. 8, the valve membrane 64 includes two valve plates 641a and 641b at two perforated regions 64a and 64b, respectively. The two valve plates 641a and 641b have the same thickness. The valve membrane 64 further includes plural extension parts 642a and 642b. The extension parts 642a and 642b are arranged around the valve plates 641a and 641b for elastically supporting the valve plates 641a and 641b. The valve membrane 64 further includes plural hollow parts 643a and 643b, each of which is formed between the two adjacent extension parts 642a and 642b respectively. When an external forces is exerted on any one of the valve plates 641a and 641b, deformation and displacement of which occur, since it is elastically supported by the extension parts 642a and 642b. Therefore, the valve structure switching between open and close states is formed, in accordance with the deformation and displacement. Preferably but not exclusively, the valve plates 641a and 641b have circular shapes, rectangular shapes, square shapes or arbitrary shapes. The valve membrane 64 further includes plural positioning holes 64c. The posts 65a of the valve chamber seat 65 are penetrated through the corresponding positioning holes 64c. Consequently, the valve membrane 64 is positioned on the valve chamber seat 65. Meanwhile, the inlet valve channel 651 and the outlet valve channel 652 are respectively covered by the valve plates 641a and 641b (see FIG. 8). In this embodiment, the valve chamber seat 65 includes two posts 65a and the valve membrane 64 includes two positioning holes 64c. It is noted that the number of the posts 65a and the number of the positioning holes 64c are not restricted.

Figure 11:
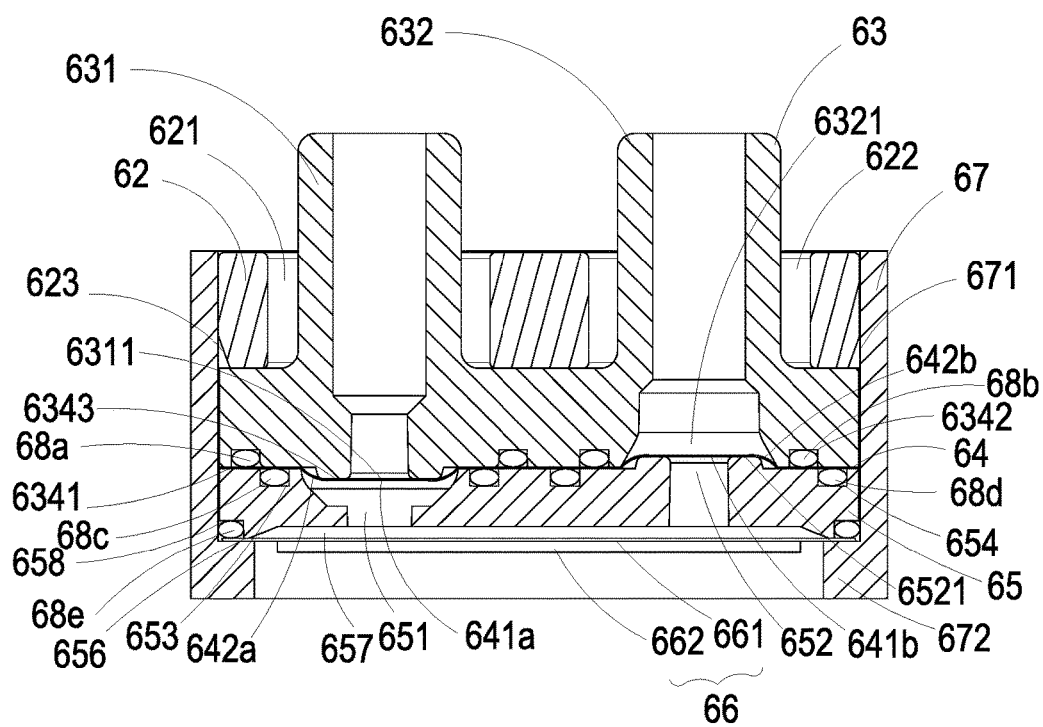
FIG. 11 is a schematic cross-sectional view illustrating the assembled structure of the fluid transportation device of FIG. 4.

FIG. 11 is a schematic cross-sectional view illustrating the assembled structure of the fluid transportation device of FIG. 4. When the valve body 63 and the valve chamber seat 65 are combined together, four sealing rings 68a, 68b, 68c and 68d are trapped in the groove 6341 of the valve body 63, the groove 6342 of the valve body 63, the groove 653 of the valve chamber seat 65 and the groove 654 of the valve chamber seat 65, respectively. Due to the sealing rings 68a, 68b, 68c and 68d, the cigarette liquid is not leaked out after the valve body 63 and the valve chamber seat 65 are combined together. The inlet passage 631 of the valve body 63 is aligned with the inlet valve channel 651 of the valve chamber seat 65. The communication between the inlet passage 631 and the inlet valve channel 651 is selectively enabled or disabled through the valve plate 641a of the valve membrane 64. The outlet passage 632 of the valve body 63 is aligned with the outlet valve channel 652 of the valve chamber seat 65. The communication between the outlet passage 632 and the outlet valve channel 652 is selectively enabled or disabled through the valve plate 641b of the valve membrane 64. When the valve plate 641a of the valve membrane 64 is opened, the cigarette liquid is transferred from the inlet passage 631 to the pressure chamber 657 through the inlet valve channel 651. When the valve plate 641b of the valve membrane 64 is opened, the cigarette liquid is transferred from the pressure chamber 657 to the outlet passage 632 through the outlet valve channel 652.

Please refer to FIGS. 5A and 5B again. The actuator 66 includes a vibration plate 661 and a piezoelectric element 662. The piezoelectric element 662 may be a square plate, and is attached on the surface of the vibration plate 661. In an embodiment, the vibration plate 661 is made of a metallic material, and the piezoelectric element 662 is made of a highly-piezoelectric material such as lead zirconate titanate (PZT) piezoelectric powder. When a voltage is applied to the piezoelectric element 662, the piezoelectric element 662 is subjected to a deformation. Consequently, the vibration plate 661 is vibrated along the vertical direction in the reciprocating manner to drive the operation of the fluid transportation device 6. In this embodiment, the vibration plate 661 of the actuator 66 is assembled with the fourth surface 656 of the valve chamber seat 65 to cover the pressure chamber 657. As mentioned above, the concave structure 658 is formed on the periphery of the fourth surface 656 outside the pressure chamber 657. For preventing from the fluid leakage, a sealing ring 68e is trapped in the concave structure 658.

As mentioned above, the valve body 63, the valve membrane 64, the valve chamber seat 65 and the actuator 66 are the main components of the fluid transportation device 6 for guiding the cigarette liquid. In accordance with the feature of the present disclosure, the fluid transportation device 6 has a specified mechanism for assembling and positioning these components. That is, it is not necessary to use the fastening elements (e.g., screws, nuts or bolts) to fasten these components. In an embodiment, the valve body 63, the valve membrane 64, the valve chamber seat 65 and the actuator 66 are sequentially stacked on each other and accommodated within the outer sleeve 67. Then, a valve cover 62 is tight-fitted into the outer sleeve 67. Consequently, the fluid transportation device 6 is assembled. The mechanism for assembling and positioning these components will be described as follows.

Figure 9:
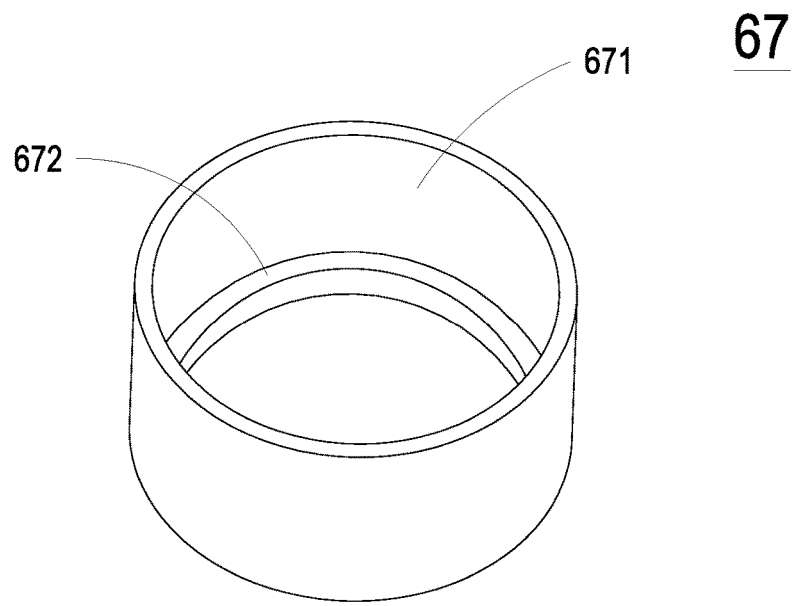
FIG. 9 is a schematic perspective view illustrating the outer sleeve of the fluid transportation device of FIG. 4.
Figure 10A:
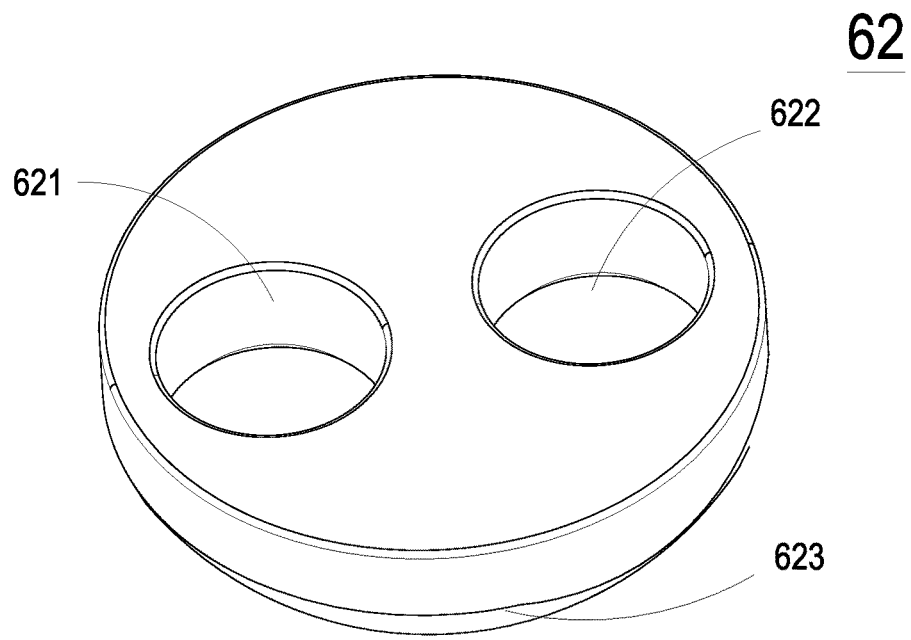
FIG. 10A is a schematic perspective view illustrating the valve cover of the fluid transportation device of FIG. 4 and taken along the front side.
Figure 10B:
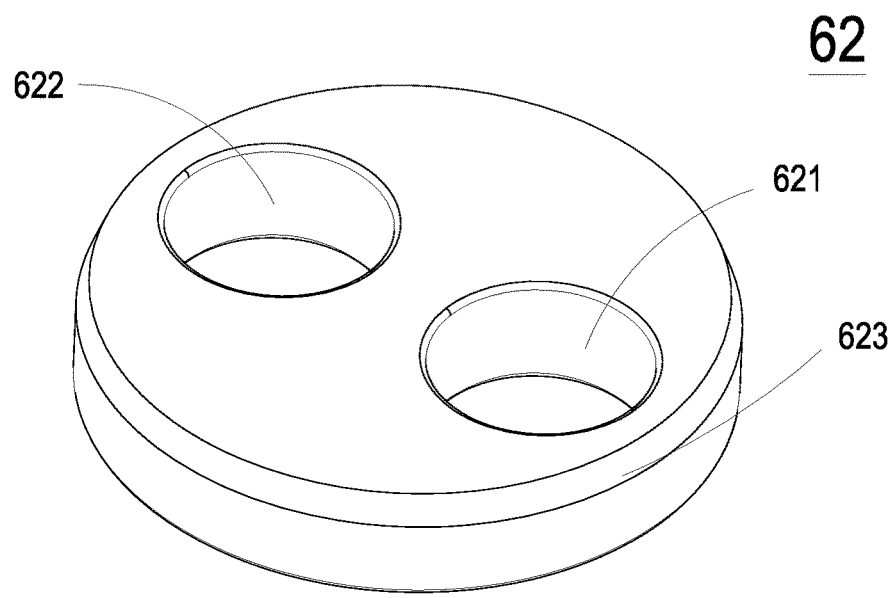
FIG. 10B is a schematic perspective view illustrating the valve cover of the fluid transportation device of FIG. 4 and taken along the rear side.

FIG. 9 is a schematic perspective view illustrating the outer sleeve of the fluid transportation device of FIG. 4. Please refer to FIGS. 5A, 5B and 9. The outer sleeve 67 is made of a metallic material. An accommodation space is defined by an inner wall 671 of the outer sleeve 67. Moreover, a ring-shaped protrusion structure 672 is formed on the lower portion of the inner wall 671 of the outer sleeve 67. Please refer to FIG. 10A and FIG. 10B. The valve cover 62 is also made of a metallic material. The valve cover 62 includes a first opening 621 and a second opening 622. The inlet passage 631 and the outlet passage 632 of the valve body 63 are penetrated through the first opening 621 and the second opening 622, respectively. Moreover, a bottom edge of the valve cover 62 has a chamfer structure 623. The outer diameter of the valve cover 62 is slightly larger than the inner diameter of the outer sleeve 67.

Please refer to FIGS. 5A and 5B again. The valve body 63, the valve membrane 64, the valve chamber seat 65 and the actuator 66 are sequentially stacked on each other and placed into the accommodation space surrounded by the inner wall 671 of the outer sleeve 67, being supported by the ring-shaped protrusion structure 672 of the outer sleeve 67. As mentioned above, the outer diameter of the valve cover 62 is slightly larger than the inner diameter of the outer sleeve 67. Because of the design of the chamfer structure 623, the valve cover 62 is tight-fitted into the outer sleeve 67. Consequently, the combination of the valve body 63, the valve membrane 64, the valve chamber seat 65 and the actuator 66 is securely fixed between the valve cover 62 and the outer sleeve 67. Therefore, the fluid transportation device 6 is assembled. In this embodiment, the actuator 66 is also disposed within the accommodation space of the outer sleeve 67. When piezoelectric element 662 is subjected to a deformation in response to the applied voltage, the vibration plate 661 is vibrated along the vertical direction in the reciprocating manner. In other words, it is not necessary to use the fastening elements (e.g., screws, nuts or bolts) to fasten the components of the fluid transportation device 6.

Please refer to FIG. 11 again. The inlet valve channel 651 of the valve chamber seat 65 is aligned with the inlet opening 6311 of the valve body 63. The inlet valve channel 651 of the valve chamber seat 65 and the inlet opening 6311 of the valve body 63 are selectively in communication with each other through the valve plate 641a of the valve membrane 64. When the inlet opening 6311 of the valve body 63 is closed by the valve plate 641a, the valve plate 641a is in close contact with the protrusion block 6343 of the valve body 63. Consequently, a pre-force is generated to result in a stronger sealing effect, thereby preventing the cigarette liquid from flowing back. Similarly, the outlet valve channel 652 of the valve chamber seat 65 is aligned with the outlet opening 6321 of the valve body 63, and the outlet valve channel 652 of the valve chamber seat 65 and the outlet opening 6321 of the valve body 63 are selectively in communication with each other through the valve plate 641b of the valve membrane 64. When the outlet valve channel 652 of the valve chamber seat 65 is closed by the valve plate 641b, the valve plate 641b is in close contact with the protrusion block 6521 of the valve chamber seat 65. Consequently, a pre-force is generated to result in a stronger sealing effect, thereby preventing the cigarette liquid from flowing back to the pressure chamber 657. In case that the fluid transportation device 6 is disabled, the fluid is not returned back to the inlet passage 631 and the outlet passage 632 of the valve body 63.

Figure 12A:
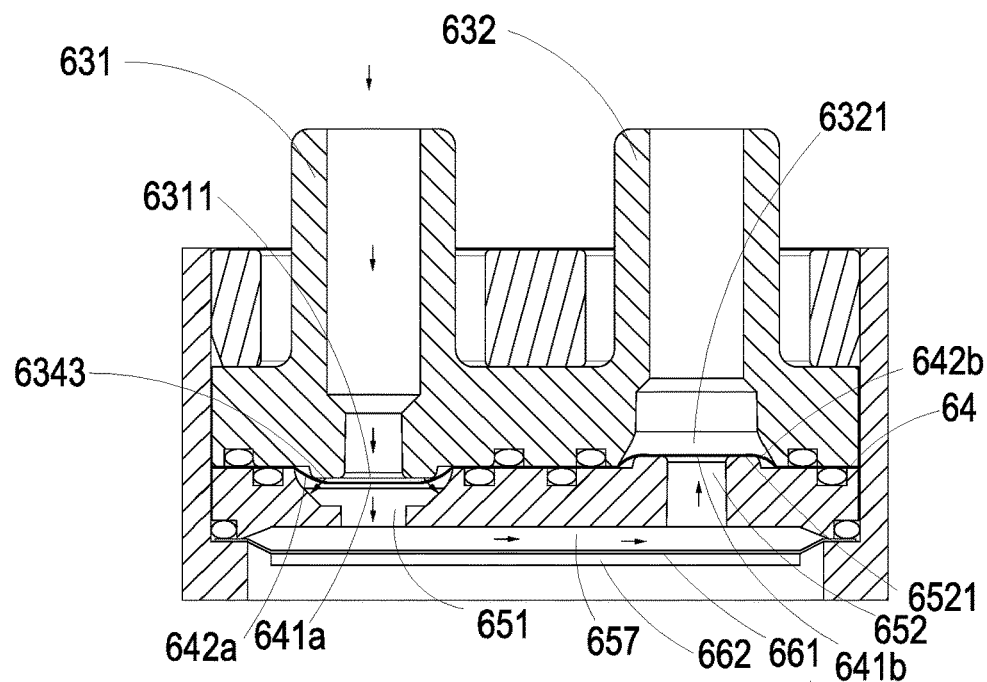
FIG. 12A is a schematic view illustrating the operations of the fluid transportation device in a first situation.

The operations of the fluid transportation device 6 will be described in more details as follows. FIG. 12A is a schematic view illustrating the operations of the fluid transportation device in a first situation. When the piezoelectric element 662 of the actuator 66 is subjected to a deformation in response to the applied voltage and causes downwardly deformation of the vibration plate 661, the volume of the pressure chamber 657 is expanded to result in suction. In response to the suction, the valve plate 641a of the valve membrane 64 is quickly opened. Consequently, a great amount of the cigarette liquid is inhaled into the inlet passage 631 of the valve body 63, and transferred to the pressure chamber 657 through the inlet opening 6311 of the valve body 63, the hollow parts 643a (see FIG. 8) of the valve membrane 64 and the inlet valve channel 651 of the valve chamber seat 65. Then, the inhaled cigarette liquid is temporarily stored in the pressure chamber 657. While the suction is also exerted on the outlet valve channel 652, the valve plate 641b supported by the extension parts 642b of the valve membrane 64 is in close contact with the protrusion block 6521 of the valve chamber seat 65 and thus the valve plate 641b is tightly closed.

Figure 12B:
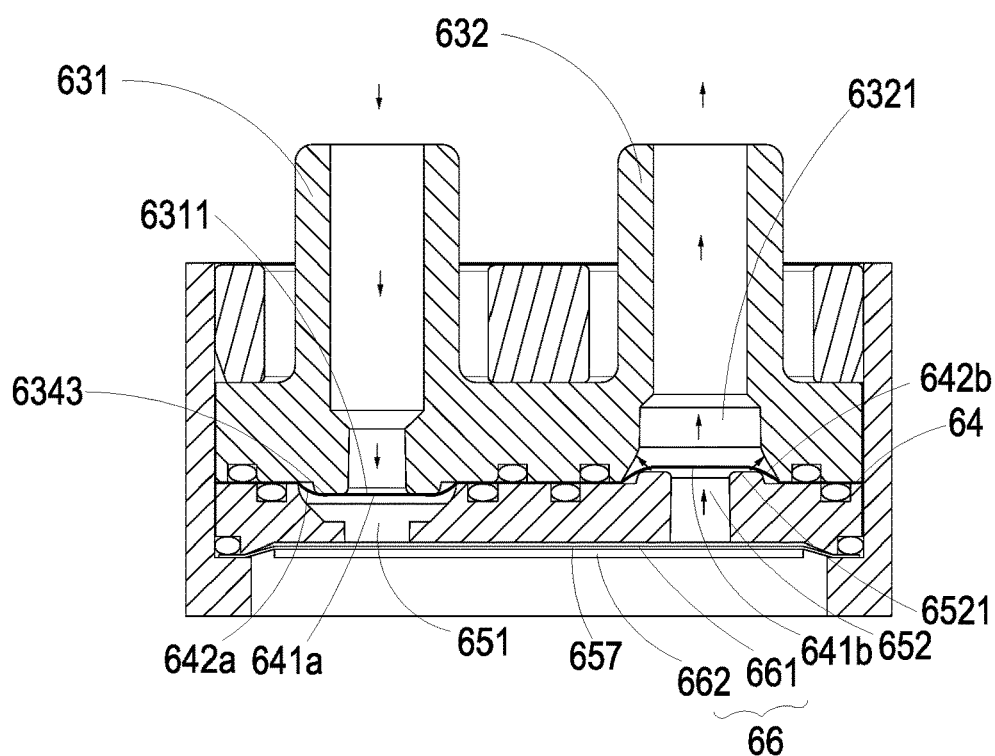
FIG. 12B is a schematic view illustrating the operations of the fluid transportation device in a second situation.

FIG. 12B is a schematic view illustrating the operations of the fluid transportation device in a second situation. Once, the direction of electric field which is applied to the piezoelectric element 662 is changed, the piezoelectric element 662 drives the vibration plate 661 to deform upwardly, the volume of the pressure chamber 657 is shrunken. As a result, the cigarette liquid within the pressure chamber 657 is compressed, and a pushing force is applied to the inlet valve channel 651. In response to the pushing force, the valve plate 641a supported by the extension parts 642a of the valve membrane 64 is in close contact with the protrusion block 6343 of the valve body 63 to be closed. Consequently, the cigarette liquid cannot be returned back to the inlet valve channel 651. Meanwhile, the pushing force is also applied to the outlet valve channel 652. In response to the pushing force, the valve plate 641b supported by the extension parts 642b of the valve membrane 64 is separated from the protrusion block 6521 to be open. Consequently, the cigarette liquid is transferred from the pressure chamber 657 to the external portion of the fluid transportation device 6 through the outlet valve channel 652 of the valve chamber seat 65, the hollow parts 643b (see FIG. 12B) of the valve membrane 64, the outlet opening 6321 of the valve body 63 and the outlet passage 632 of the valve body 63, sequentially. The processes of FIGS. 12A and 12B are repeatedly done. Consequently, the cigarette liquid can be transferred by the fluid transportation device 6 at high efficiency without being returned back.

The fluid transportation device 6 is supported and positioned in the second casing 1b through the supporting seat 1e. Moreover, the fluid transportation device 6 is located at the bottom portion of the liquid storage component 5. The inlet passage 631 and the input channel 6a of the fluid transportation device 6 are connected with each other. The fluid transportation device 6 is in communication with the liquid storage component 5 through the input channel 6a. The outlet passage 632 and the output channel 6b of the fluid transportation device 6 are connected with each other. The output channel 6b is in communication with the input port 441 of the liquid guiding tube 44 of the atomization component 4 through the liquid transfer tube 6c. Consequently, the cigarette liquid can be transmitted to the liquid guiding tube 44 by the fluid transportation device 6 and outputted from the liquid guiding tube 44 through the perforations 442. When the fluid transportation device 6 is enabled by the control board 22, the fluid transportation device 6 is used as a switch element. Consequently, the cigarette liquid is transferred from the liquid storage component 5 to the liquid guiding tube 44 through the fluid transportation device 6 at a fixed quantity. Under the same pressure, the cigarette liquid is uniformly transferred to the liquid guiding tube 44 through the perforations 442 to generate uniform droplets. Once the cigarette liquid outside the liquid guiding tube 44 reaches a saturation state, the fluid transportation device 6 is disabled. In other words, the cooperation of the fluid transportation device 6 and the atomization component 4 forms a controllable switch element such that the amount of the cigarette liquid to be transferred to the atomization component 4 can be precisely controlled. Consequently, the taste of the atomized vapor is enhanced, and the liquid leakage problem is solved.

The operations of the electronic cigarette will be described as follows. When the user inhales the air through the bore 92 of the mouthpiece 9, the airflow flows through the electronic cigarette. According to the sensing result of the sensing unit 3, the electric circuit of the electronic cigarette is enabled. Consequently, the electric heater 41 is enabled to heat the cigarette liquid. When the user stops inhaling, the airflow does not flow through the electronic cigarette. According to the sensing result of the sensing unit 3, the electric circuit of the electronic cigarette is disabled. Meanwhile, the electric heater 41 is disabled. The cooperation of the fluid transportation device 6 and the atomization component 4 forms a controllable switch element which precisely controls the amount of the cigarette liquid to be transferred from the liquid storage component 5 to the liquid guiding tube 44 through the fluid transportation device 6 at a fixed quantity. More specifically, when the user inhales the air through the bore 92 of the mouthpiece 9, the airflow flows through the electronic cigarette. According to the sensing result of the sensing unit 3, the driving module 2 may supply electric power to the heater module 212 to initiate the electric heater 41, and maintain the fixed quantity of the cigarette liquid to be transferred at the same time. After the cigarette liquid is heated by the electric heater 41, the atomized vapor is generated. Consequently, the user inhales the atomized vapor from the passageway 51 of the liquid storage component 5 through the opening 92 of the mouthpiece 9.

When the user inhales the atomized vapor through the bore 92 of the mouthpiece 9, the air pressure sensor 32 issues the control signal according to the result of detecting the pressure of the airflow. According to the control signal, the driving frequency of the fluid transportation device 6 and the driving frequency of the electric heater 41 are changed. Consequently, the speed of providing the cigarette liquid from the fluid transportation device 6 and the speed of atomizing the cigarette liquid by the electric heater 41 are adjusted. Consequently, the user can inhale a great amount of atomized vapor quickly and inhale the same amount and concentration of atomized vapor.

From the above descriptions, the present disclosure provides a driving module for an electronic cigarette. The cooperation of the fluid transportation device and the atomization component forms the controllable switch element. The amount of the cigarette liquid to be transferred to the atomization component is precisely controlled by the controllable switch element. The electronic cigarette includes an airflow sensor and an air pressure sensor. The air pressure sensor issues a control signal to a control board of the driving module according to the result of detecting the pressure of the airflow. According to the control signal, the control board controls the power board to calculate a specified voltage value. After the specified voltage value is calculated, the voltage of the driving power is converted into the specified voltage, and a driving signal is generated according to the specified voltage. According to the driving signal, the driving power with the specified voltage value is provided to the fluid transportation device through the fluid driving unit to enable the fluid transportation device to transfer the cigarette liquid to the atomization component, and the driving power with the specified voltage value is provided to the atomization component through the heater module to enable the atomization component to atomize the cigarette liquid and generate an atomized vapor. When the user stops smoking, the airflow does not flow through the electronic cigarette. According to the sensing result of the sensing unit, the electric circuit of the electronic cigarette is disabled. Meanwhile, the electric heater is disabled. According to the control signal, the driving frequency of the fluid transportation device and the driving frequency of the electric heater are changed. Consequently, the speed of providing the cigarette liquid from the fluid transportation device and the speed of atomizing the cigarette liquid by the atomization component are adjusted. Meanwhile, the cigarette liquid can be transferred by the fluid transportation device at high efficiency without being returned back. Since the amount of the liquid cigarette is precisely controlled, the droplets are uniformly generated, the taste of the atomized vapor is enhanced, and the liquid leakage problem is solved.

While the invention has been described in terms of what is presently considered to be the most practical and preferred embodiments, it is to be understood that the invention needs not be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:

1. A driving module for an electronic cigarette containing a cigarette liquid, the electronic cigarette comprising a casing, a mouthpiece, a sensing unit, an atomization component, a liquid storage component and a fluid transportation device, the driving module comprising:
   a battery for providing a driving power to the electronic cigarette;
   a connection interface electrically connected with the battery;
   a power board electrically connected with the battery through the connection interface, and comprising a voltage converter, a heater module and a voltage controller, wherein the voltage converter is configured to adjust the magnitude of the voltage of the driving power, the heater module is configured to drive the atomization component to heat and atomize the cigarette liquid, and the voltage controller is configured to calculate a specified voltage value; and
   a control board electrically connected with the battery through the connection interface, and comprising a microprocessor and a fluid driving unit, wherein the microprocessor receives a control signal and issues a driving signal, and the fluid driving unit drives the fluid transportation device to transfer the cigarette liquid according to the driving signal,
   wherein when the microprocessor receives the control signal, the microprocessor controls the voltage controller to calculate the specified voltage value according to the control signal and the voltage converter to convert a voltage of the driving power provided by the battery into the specified voltage, and the microprocessor issues the driving signal to the fluid driving unit and the heater module such that the driving power with the specified voltage value is provided to the fluid transportation device and the atomization component by the fluid driving unit and the heater module respectively, thereby enabling the fluid transportation device to transfer the cigarette liquid to the atomization component which atomizes the cigarette liquid to generate an atomized vapor.

2. The driving module for the electronic cigarette according to claim 1, wherein the casing of the electronic cigarette is an assembly of a first casing and a second casing, wherein the battery is disposed within the first casing, and the sensing unit, the liquid storage component, the fluid transportation device, the atomization component, the connection interface, the power board and the control board are disposed within the second casing, wherein the first casing and the second casing are assembled and electrically connected with each other through the connection interface.

3. The driving module for the electronic cigarette according to claim 1, wherein the electronic cigarette further comprises a bracket disposed within the casing and connected with an inner wall of the casing, thereby providing a supporting force to the atomization component.

4. The driving module for the electronic cigarette according to claim 1, wherein the battery of the driving module for the electronic cigarette is a disposable battery.

5. The driving module for the electronic cigarette according to claim 1, wherein the battery of the driving module for the electronic cigarette is a rechargeable battery.

6. The driving module for the electronic cigarette according to claim 1, wherein the electronic cigarette further comprises a light emitting diode.

7. The driving module for the electronic cigarette according to claim 6, wherein the light emitting diode of the electronic cigarette is located at an end of the casing, and selectively in an on state or an off state under control of the control board to provide a prompt message for operation.

8. The driving module for the electronic cigarette according to claim 6, wherein the light emitting diode of the electronic cigarette is located at an end of the casing and a luminance of the light emitting diode is adjusted under control of the control board to indicate a flow condition of the atomized vapor.

9. The driving module for the electronic cigarette according to claim 1, wherein the sensing unit of the electronic cigarette comprises an airflow sensor and an air pressure sensor, wherein the electronic cigarette is selectively enabled or disabled according to a result of detecting an airflow by the airflow sensor, and the air pressure sensor issues the control signal according to a result of detecting a pressure of the airflow, wherein according to the control signal, a driving frequency of the fluid transportation device and a driving frequency of the heater module are changed, so that a speed of providing the cigarette liquid from the fluid transportation device and a speed of atomizing the cigarette liquid by the atomization component are adjusted.

10. The driving module for the electronic cigarette according to claim 1, wherein the atomization component comprises an electric heater and a liquid guiding tube, wherein the liquid guiding tube is made of stainless steel.

11. The driving module for the electronic cigarette according to claim 1, wherein the atomization component comprises an electric heater and a liquid guiding tube, wherein the liquid guiding tube is made of a heat-resistant material.

12. The driving module for the electronic cigarette according to claim 1, wherein the mouthpiece of the electronic cigarette further comprises a filter, the filter seals a connecting opening between the mouthpiece and the casing to form a preventive measure from inhalation, whereby the cigarette liquid is blocked by the filter when being initially heated and incompletely atomized.

13. The driving module for the electronic cigarette according to claim 1, wherein the fluid transportation device further comprises:
   a valve body comprising an outlet passage, an inlet passage, a first surface and a second surface, wherein the inlet passage and the outlet passage run through the first surface and the second surface, an inlet opening is formed on the second surface and in communication with the inlet passage, and an outlet opening is formed on the second surface and in communication with the outlet passage;
   a valve membrane comprising two valve plates, plural extension parts and plural hollow parts, wherein the two valve plates have the same thickness, the plural extension parts are arranged around the valve plates for elastically supporting the valve plates, and the hollow parts are arranged between the extension parts;
   a valve chamber seat comprising a third surface, a fourth surface, an inlet valve channel, an outlet valve channel and a pressure chamber, wherein the inlet valve channel and the outlet valve channel run through the third surface and the fourth surface, the two valve plates are supported on the inlet valve channel and the outlet valve channel, the pressure chamber is concavely formed on the fourth surface, and the pressure chamber is in communication with the inlet valve channel and the outlet valve channel; and
   an actuator, wherein the pressure chamber of the valve chamber seat is covered by the actuator, wherein the valve body, the valve membrane, the valve chamber seat and the actuator are sequentially stacked on each other, wherein while the actuator is enabled, the cigarette liquid is fed into the inlet passage and outputted from the outlet passage.

14. The driving module for the electronic cigarette according to claim 13, wherein plural recesses are formed on the second surface of the valve body, and plural posts are formed on the third surface of the valve chamber seat, wherein the plural posts are inserted into the plural recesses correspondingly, whereby the valve chamber seat is fixed on the valve body.

15. The driving module for the electronic cigarette according to claim 14, wherein the valve membrane is arranged between the valve body and the valve chamber seat, and the valve membrane comprises plural positioning holes corresponding to the plural posts, wherein the plural posts are penetrated through the corresponding positioning holes, whereby the valve membrane is positioned and supported on the valve chamber seat.

16. The driving module for the electronic cigarette according to claim 13, wherein a first groove is formed on the second surface and arranged around the inlet opening, a second groove is formed on the second surface and arranged around the outlet opening, a third groove is formed on the third surface and arranged around the inlet valve channel, and a fourth groove is formed on the third surface and arranged around the outlet valve channel, wherein the fluid transportation device further comprises plural sealing rings, and the plural sealing rings are trapped in the first groove, the second groove, the third groove and the fourth groove, respectively.

17. The driving module for the electronic cigarette according to claim 13, wherein a first protrusion block is formed on the second surface of the valve body and disposed on a periphery of the inlet opening, and a second protrusion block is formed on the third surface and disposed on a periphery of the outlet valve channel, wherein the first protrusion block and the second protrusion block are cooperated with the two valve plates respectively to form pre-forces for sealing and preventing the cigarette liquid from returning back.

18. The driving module for the electronic cigarette according to claim 13, wherein the actuator comprises a vibration plate and a piezoelectric element, wherein the piezoelectric element is attached on a surface of the vibration plate, the piezoelectric element is subjected to a deformation in response to an applied voltage, and the vibration plate of the actuator is assembled with the fourth surface of the valve chamber seat to cover the pressure chamber.

19. The driving module for the electronic cigarette according to claim 13, wherein the fluid transportation device comprises:
a valve cover having a first opening and a second opening; and
an outer sleeve having an accommodation space surrounded with an inner wall of the outer sleeve, wherein a ring-shaped protrusion structure is formed on the inner wall of the outer sleeve, and wherein the valve body, the valve membrane, the valve chamber seat and the actuator are sequentially stacked on each other, accommodated within the accommodation space of the outer sleeve, and supported on the ring-shaped protrusion structure, wherein the inlet passage and the outlet passage of the valve body are respectively penetrated through the first opening and the second opening of the valve cover.

* * * * *